(12) United States Patent
Nobis et al.

(10) Patent No.: US 8,167,877 B2
(45) Date of Patent: May 1, 2012

(54) ENDOSCOPIC MUCOSAL RESECTION DEVICE WITH OVERTUBE AND METHOD OF USE

(75) Inventors: Rudolph Nobis, Mason, OH (US); Michael Clem, Maineville, OH (US); Christopher J. Hess, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1348 days.

(21) Appl. No.: 11/625,837

(22) Filed: Jan. 23, 2007

(65) Prior Publication Data

US 2007/0118166 A1 May 24, 2007

Related U.S. Application Data

(63) Continuation of application No. 10/673,928, filed on Sep. 29, 2003, now Pat. No. 7,169,115.

(51) Int. Cl.
*A61B 18/14* (2006.01)
*A61B 10/00* (2006.01)
(52) U.S. Cl. ............ 606/45; 606/48; 600/566; 600/567
(58) Field of Classification Search .................. 606/37, 606/41, 46, 170–171
See application file for complete search history.

(56) References Cited

U.S. PATENT DOCUMENTS

| 4,116,198 A | 9/1978 | Roos |
| 6,019,733 A | 2/2000 | Farascioni |
| 6,214,024 B1 | 4/2001 | Houser |
| 6,432,064 B1 * | 8/2002 | Hibner et al. ............... 600/564 |
| 6,872,204 B2 * | 3/2005 | Houser .......................... 606/37 |
| 7,169,115 B2 | 1/2007 | Nobis et al. |
| 2003/0009085 A1 | 1/2003 | Arai et al. |

FOREIGN PATENT DOCUMENTS

| GB | 2365340 A | 2/2002 |
| JP | 2001-321389 | 11/2001 |
| WO | WO 01/89370 A | 11/2001 |
| WO | WO 02/35986 A | 5/2002 |

OTHER PUBLICATIONS

EPO Search Report dated Jan. 12, 2005 for corresponding patent application, European Patent Application No. EP 04 25 5975.

* cited by examiner

*Primary Examiner* — Roy Gibson

(57) ABSTRACT

A medical apparatus and method useful for resecting tissue from the gastrointestinal tract are disclosed. The apparatus can include an RF tissue cutting device disposed inward of a side opening in the device. A tissue stop can be used to control the depth of tissue resected, and the tissue stop can include holes for communicating vacuum for drawing tissue into the side opening. The tissue stop can be electrically grounded with respect to the RF tissue cutting device, and the tissue stop can provide one pole of an RF electrical circuit.

4 Claims, 11 Drawing Sheets

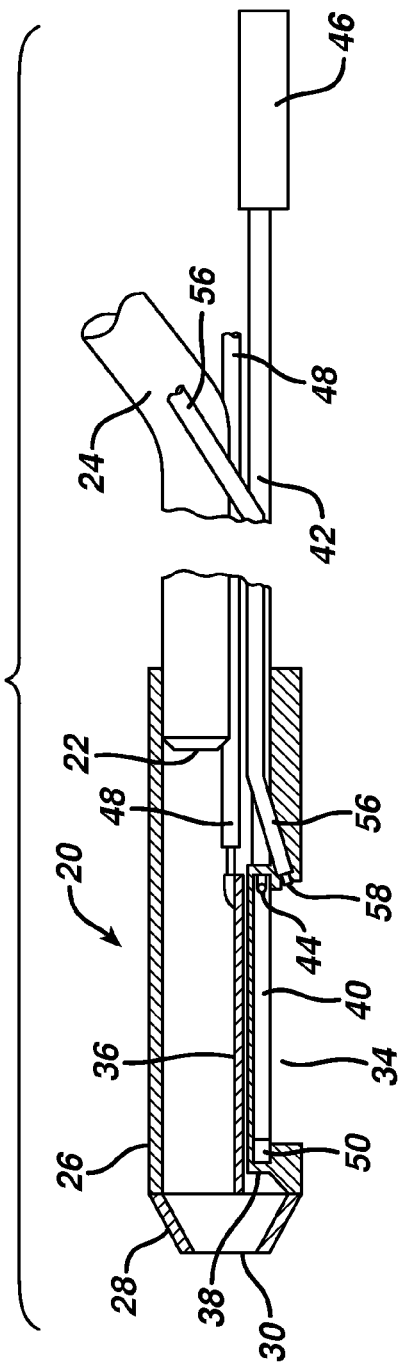

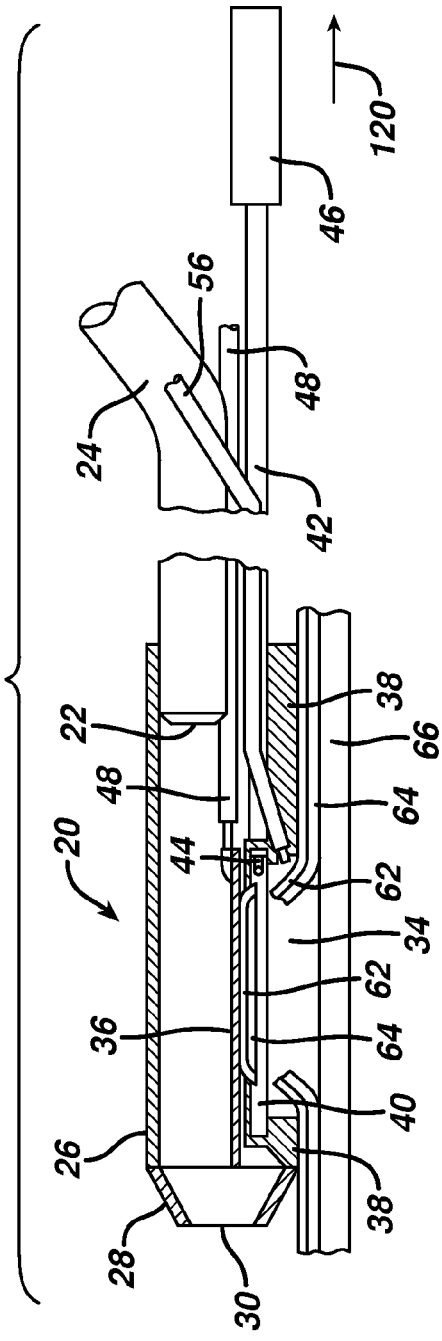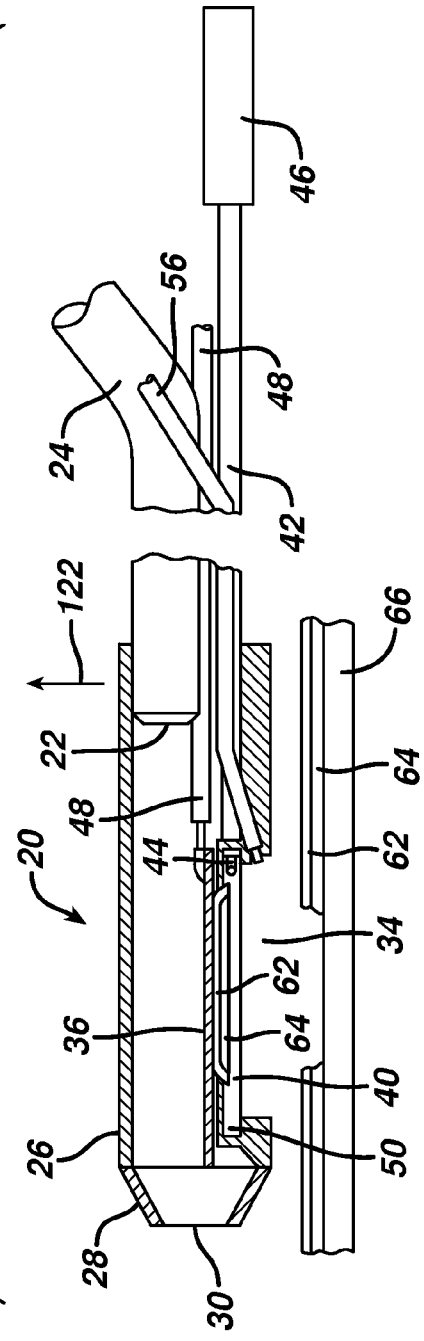

ENDOSCOPIC MUCOSAL RESECTION DEVICE WITH OVERTUBE AND METHOD OF USE

This application is a continuation application of, and claims priority to, allowed U.S. patent application Ser. No. 10/673,928 filed Sep. 29, 2003 now U.S. Pat. No. 7,169,115 and published as US2005/0070763, which application and publication are incorporated herein by reference.

FIELD OF THE INVENTION

The present invention is related generally to endoscopy and more particularly to endoscopic mucosal resection.

BACKGROUND OF THE INVENTION

Cancerous or benign lesions of the GI tract often start in the mucosal layer of the stomach or intestines. With improved diagnostics and screening, such lesions are being identified prior to extension into the wall of the stomach or intestines. Unfortunately, definitive therapy has historically involved invasive surgical resection of the lesion and adjacent bowel. Treatment of such early lesions by local excision of the mucosal, with access via natural orifices, would represent a far less invasive approach.

Existing approaches to local mucosal resection have utilized a variety of endoscopic instruments. Current methods can be described as "suck and cut" or "lift and cut". In the suck and cut method, a chamber attached to the end of the endoscope is placed near the lesion, suction is applied to draw the lesion into the chamber, an electrosurgical snare within the chamber is then activated to excise the entrapped tissue. This is done repeatedly to completely resect the affected tissue. In the lift and cut method, a two-channel endoscope is used. Through one channel of the endoscope a grasper is passed to lift the lesion. An electrosurgical snare, passed through the other endoscope channel is placed around the shaft of the grasper and advanced to encircle the lifted tissue. The snare is then activated to excise the tissue. Both approaches are commonly preceded by injecting saline or other solutions under the mucosal to raise the lesion away from the underlying muscle wall in an effort to limit perforation. This lesion, common in the art, is known as a "bleb".

UK Patent Application GB 2365340A to Appleyard and Swain discloses a tissue resection device for removing tissue with a cavity of variable volume, which patent application is incorporated herein by reference Other devices and methods have been proposed for providing resection of tissue. Still, scientists and engineers continue to seek improved methods for the resection of tissue in the gastro-intestinal tract.

SUMMARY OF THE INVENTION

The present invention provides an apparatus which can employ suction to engage mucosal tissue for resection. In contrast to some existing devices which use suction for endoscopic mucosal resection, the suction chamber of the present device can open laterally, or on the side of apparatus corresponding to the long axis of the endoscope. Accordingly, the present invention can employ a suction opening which extends generally parallel to the long axis of the endoscope. Existing devices which employ an opening which is at the distal end of the device have the plane of the suction opening being substantially perpendicular to the long axis of the endoscope.

Once tissue is drawn into the resection chamber, an electrosurgical wire can be used for transection. In contrast to the flexible electrosurgical snares used in existing devices, the present invention can employ a relatively rigid wire positioned within the device to be drawn across or pushed across the chamber opening to excise the entrapped tissue. The wire is only electrically active over the portion, which is exposed, non insulated, to the chamber opening. The present invention can also include a flexible, electrically conductive tissue stop, which can function to limit the depth of tissue that can enter the suction chamber for resection. Such a tissue stop can provide for greater safety of resection by reducing risk of alimentary canal perforation and reducing patient burns from monopolar ground pads. The tissue stop can also be perforated for communicating vacuum.

In one embodiment, the present invention provides a medical apparatus comprising a body with an outer surface having a side opening, the side opening for receiving tissue therethrough; a cutter adapted to receive energy for cutting tissue, the cutter disposed inward of the opening and adapted to traverse a length of the side opening for cutting tissue extending through the side opening; and a tissue stop disposed inward of the side opening and the cutter, the tissue stop having at least one opening therethrough for conveying vacuum to draw tissue through the side opening. The tissue stop can comprise a plurality of openings therethrough for conveying vacuum.

In another embodiment, the present invention provides a method comprising the steps of providing a source of vacuum, positioning a perforated tissue stop in the gastro-intestinal tract; drawing tissue against the perforated tissue stop in the gastro-intestinal tract; and cutting a tissue sample from the tissue drawn against the perforated tissue stop.

In another embodiment, the present invention provides a medical apparatus comprising: an overtube for receiving an endoscope therein, the overtube comprising a side opening for receiving tissue therethrough; and a tissue sample device disposed in the overtube, the tissue sample device comprising a tissue cutter adapted to traverse a length of the side opening for severing a tissue sample from tissue extending into the side opening.

In another embodiment, the present invention provides a method for obtaining a tissue sample comprising: providing an endoscope; providing an overtube having a side opening and a tissue cutter; inserting the overtube into a patient's body with the endoscope; receiving tissue into the side opening of the overtube; and cutting tissue extending into the side opening with the tissue cutter.

In another embodiment, the present invention provides a medical apparatus comprising: an outer surface having a side opening, the side opening for receiving tissue therethrough; a cutter adapted to receive RF energy for cutting tissue, the cutter supported inward of the side opening and adapted to traverse a length of the side opening for cutting tissue extending through the side opening; and a tissue stop disposed inward of the cutter; wherein the tissue stop comprises a pole of the RF circuit.

In another embodiment, the present invention provides a method of cutting tissue comprising the steps of positioning an RF cutting device in the gastro-intestinal tract of a patient; positioning a tissue stop in the gastro-intestinal tract; positioning a tissue mass against the tissue stop; energizing the RF cutting device; grounding the tissue stop; and cutting a tissue sample from the tissue mass.

BRIEF DESCRIPTION OF THE FIGURES

FIG. 9 is a cross-sectioned side elevation view similar to FIG. 8, showing a cutting mechanism retracted rearwardly of the aperture into a shear slot.

FIG. 10 is a cross-sectioned side elevation view similar to FIG. 8, with the addition of tissue shown adjacent the aperture, and a saline solution injection needle extended to enter the tissue to form a bleb.

FIG. 13 is a cross-sectioned side elevation view similar to FIG. 12, showing completion of cutting while vacuum holds the mucosal and sub-mucosal tissue to the underside of the stop plate.

FIG. 14 is a cross-sectioned side elevation view similar to FIG. 13, showing the removal of the cutter support from the muscularis tissue after the cut has been completed.

DETAILED DESCRIPTION OF THE INVENTION

Figure 3:
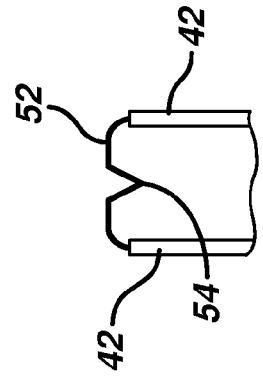
FIG. 3 is a plan view of an alternative cutting element.

With reference to FIGS. 1, 2, 7 & 8, one embodiment of a cutting device 20 of the present invention is shown attached to a distal end 22 of a commercially available endoscope. Endoscope 24 may be made by Olympus Optical, having an outside diameter of about 0.2 to 0.7 inches: Cutting device 20 can have a rigid or semi-rigid cylindrical cutter support 26 which is attached to the endoscope perimeter by any suitable means, such as by shrink wrap, adhesive, snap fit, press fit, threaded engagement, or other suitable means known in the art for connecting one generally hollow member to another along parallel longitudinal axes.

Distal end 22 of endoscope 24 can be located at one end of cutter support 26. A flexible conical member 28 can be attached to the opposite, distal end of cutter support 26. Conical member 28 can be employed to provide for a smooth entry of cutting device 20 into the alimentary canal of a patient. Conical member 28 can have an open distal end 30 of about 0.3 inches in diameter through which tooling, not shown, from a working channel 32 of endoscope 24 may extend, and through which unobstructed camera vision of the inside of the patient's alimentary canal is obtained. Conical member 28 can have an open distal end 30 which permits passage of the distal end of the endoscope 24 therethrough.

Conical member 28 can be made of a flexible polymer, such as polyvinylchloride (PVC), polyethylene terephthalate (PET), or other suitable flexible materials. Conical member 28 can be attached to cutter support 26 by threading it thereon, polymer welding, press fit, snap-fit, or other means well known in the art. Conical member 28 can be coaxial with cutter support 26, whereas a longitudinal axis of endoscope 24 can be offset from a longitudinal axis of cutter support 26.

Cutter support 26 can be generally cylindrical in shape, and can have an outer diameter of between about 0.50 and 0.75 inch, and an axial length of between about 1.0 and about 1.50 inch. In one embodiment, cutter support 26 can have an outer diameter of about 0.60 inches and an axial length of about 1.25 inches. Cutter support 26 can be formed of a transparent polymer, such as polycarbonate or PVC.

Cutter Support 26 also can employ a lateral tissue receiving aperture 34. Aperture 34 can have any suitable shape, and in the embodiment shown is generally rectangular when viewed straight on, and is positioned along one side of the cutter support 26. The lateral tissue receiving aperture 34 can be about 0.60 to 1.00 inches long (as measured parallel to the axial length of the cutter support 26), and about 0.30 to 0.50 inches wide (as measured around the circumference of the outside surface of the cutter support 26).

A perforated tissue stop plate 36 can be disposed radially inward from tissue receiving aperture 34, to be positioned inward of tissue receiving aperture 34. Tissue stop plate 36 can be injection molded to the inner wall of cutter support 26, or alternatively, made separately and otherwise fixedly attached to the inner wall of cutter support 26. Stop plate 36 can be semi-rigid, and can be deformable. In one embodiment, stop plate 36 can be formed and attached to cutter support 26 so that stop plate 36 can take on a first configuration (such as an outwardly bowed, generally arcuate configuration), and a second configuration at least a portion of the tissue stop plate is drawn or otherwise deformed or deflected inward (such as by vacuum) to receive tissue through the aperture 34. Stop plate 36 can be, in whole or in part, transparent, and can be made of or comprise a conductive material. For instance, stop plate 36 can be formed of a polymer or biocompatible metal which is conductive, or a polymer having a conductive ink applied thereto, or can include a generally transparent base layer with a conductive outer layer having openings therethrough, such as in the form of a grid pattern.

Figure 1:
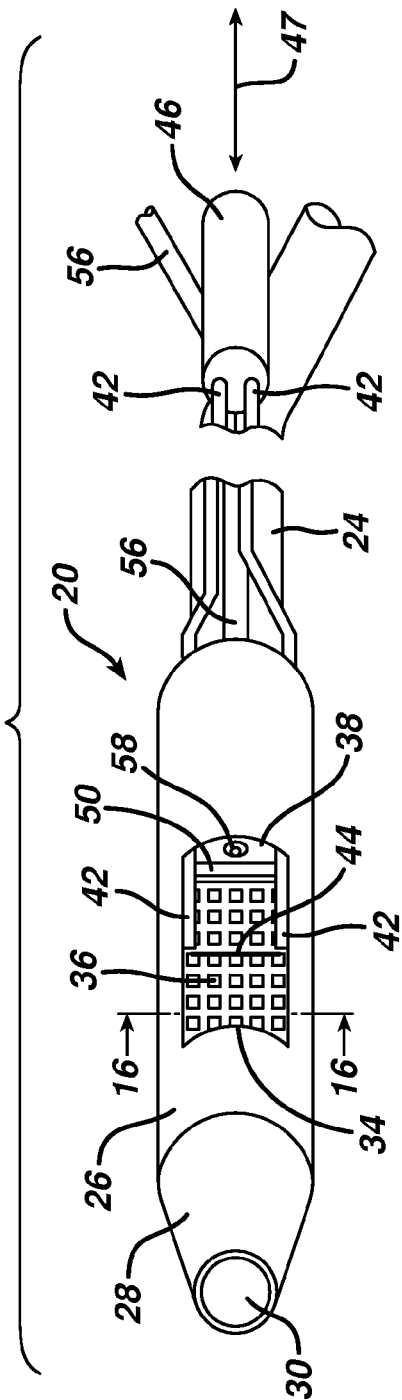
FIG. 1 is a perspective view of a cutting device, showing a cutter support attached to a distal end of an endoscope, and features internal to the cutter support.

In FIG. 1, stop plate 36 is shown having a plurality of perforations therethrough. Perforations in stop plate 36 can be employed to provide openings through the thickness of the stop plate 36, and to communicate vacuum from a source of vacuum to draw tissue into the tissue receiving aperture 34. In one embodiment, the perforations in the stop plate 36 can be about 0.03 to 0.10 inches in diameter and spaced about 0.10 to 0.30 inches apart. While circular perforations are shown, other suitable shapes, including rectangular, square, elliptical, or oval shapes can be employed.

Cutter support 26 can have a support 38 molded therein, which contains rectangular wire guide slots 40 (FIG. 2) which can be located parallel to the long edges of aperture 34 on opposite sides of aperture 34. Guide slots 40 can be disposed outward of stop plate 36, and inward of aperture 34. Wire guide slots 40 are sized for wire insulating sleeves 42 to slide longitudinally therein. Insulating sleeves 42 surround two wires that extend from a heating source to distal ends of slots 40 near conical member 28, where they are attached to a heatable (such as by RF energy) cutting element 44. Cutting element 44 extends from the sleeves 42 across aperture 34. As the wires and sleeves 42 are moved parallel to the longitudinal axis of cutter support 26 within slots 40, cutting element 44 passes across aperture 34 and cuts tissue drawn into aperture 34.

Cutting element 44 can be in the form of a straight wire filament about 0.01 to about 0.04 inches diameter, a flat blade about 0.01 inches thick and 0.03 inches deep, a braided wire about 0.01 to about 0.04 inches in diameter, or other suitable tissue cutting devices. Such cutting element configurations can be about 0.50 inches wide to in order to span aperture 34, and can be made of a material capable of being heated, such as by radio frequency (RF) energy. Suitable materials from which cutting element 44 can be formed when used with RF energy include electrically conductive materials including without limitation, steel, steel alloys, titanium, or titanium alloys.

Cutting element 44 may be heated by a number of heating means including conduction and RF heating, which are commonly known in the endoscopic cutting art. Wire sleeves 42 can be formed of electrical insulating material such as teflon and can be about 0.03 inches in diameter. Electrically conducting wires and their sleeves 42 can extend along the outside of endoscope 24 to an insulated slide block 46. Block 46 can be is slidably attached to a handle located along side an endoscope operating handle. Sleeves 42 can be slidably attached at multiple places to endoscope 24 along its length. Slide block 46 can be supported to move longitudinally according to arrow 47 in FIG. 1, to extend and retract sleeves 42 along endoscope 24 and through wire guide slots 40 so that cutting element 44 may be moved past the entire length of aperture 34. Moving block 46 in a distal direction moves cutting element 44 across the length of aperture 34 in a distal direction, while moving block 46 in a proximal direction moves cutting element across the length of aperture 34 in a proximal direction.

For RF heating embodiments, an RF generator can be connected to the wires attached to the cutting element via a switching mechanism to deliver a wattage range of from about 10 to about 150 watts at a suitable frequency, such as a frequency of between about 300 kiloHertz to 3 megaHertz, thereby rapidly heating cutting element 44 to a temperature from about 60° C. to about 120° C. whenever heating is desired. In one embodiment, an Erbe 300 brand generator can be used with the following settings in monopolar or bipolar mode: pure cut, 40 Watts.

Figure 2:
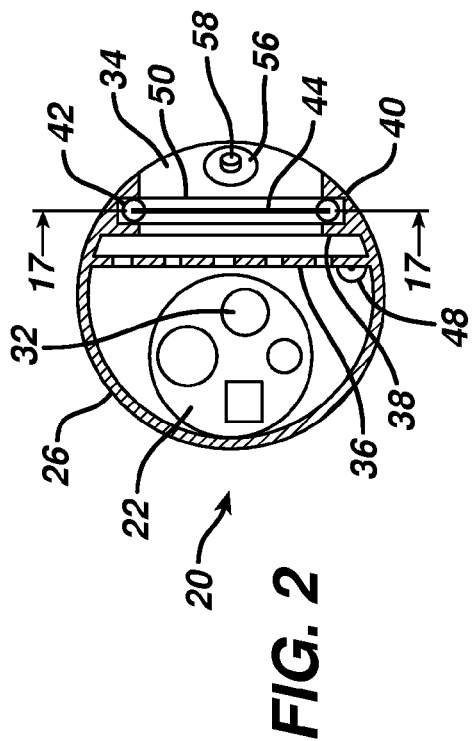
FIG. 2 is a cross-sectioned end view of the cutter support of FIG. 1, taken along section line 16-16, showing a circular embodiment of the cutter support and its internal features.

In an RF heating embodiment an RF grounding plate or pad is typically located outside a patient's body. However, in the present invention an RF grounding plate may be located within cutting device 20, for example, by forming tissue stop plate 36 of a conducting material, or disposing a conductor on using tissue stop plate 36 as a metal or metallized electrical grounding plane. FIG. 2 shows an attachment of a ground wire 48 to the edge of stop plate 36. Ground wire 48 extends along side endoscope 24 to a ground, not shown, attached to the RF generator. Accordingly, the cutting device 20 can provide an electrical configuration which cutting element 44 provides one pole, and the tissue stop plate 36 provides the other pole.

Figure 7:
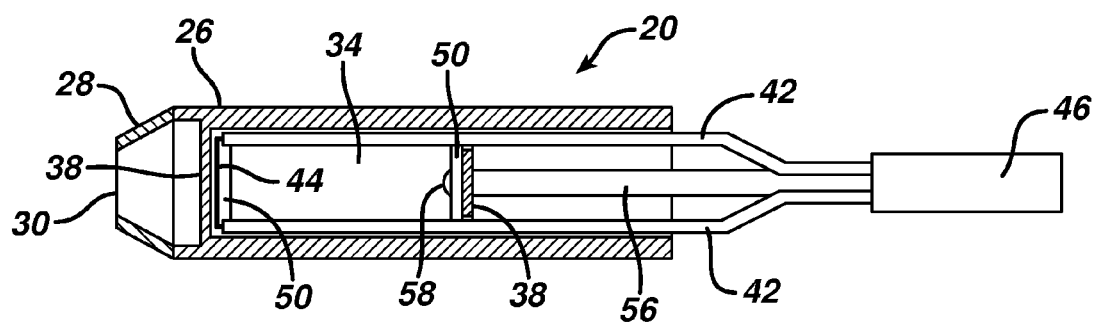
FIG. 7 is a cross-sectioned top plan view of the cutter support of FIG. 1, taken along section line 17-17 of FIG. 2, showing a cutting mechanism extended forward of an aperture in the cutter support.
Figure 8:
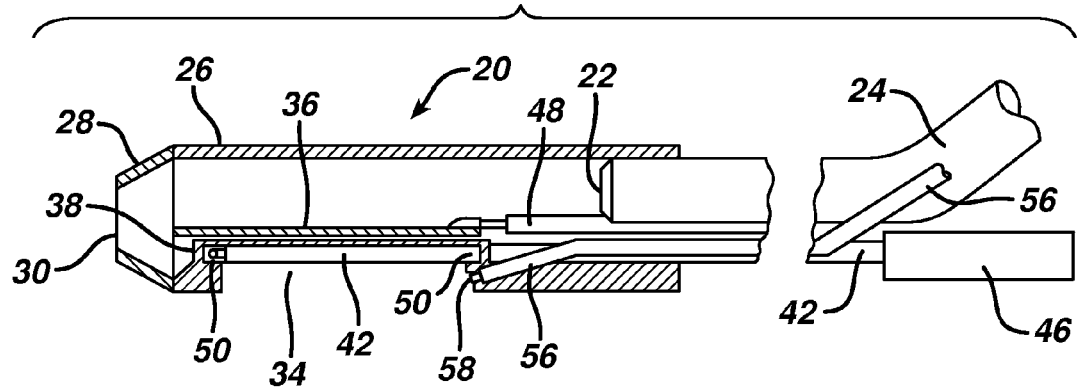
FIG. 8 is a cross-sectioned side elevation view of the cutter support of FIG. 1, sectioned through the longitudinal axis thereof, showing a perpendicular view of the features of FIG. 7.

Support 38 for wire slots 40 can also include at one or both ends of the wire slots a cutting element shear slot 50, into which cutting element 44 moves at the end of a cutting stroke in order to strip tissue from the cutting element. With shear slots 50 located at both ends of aperture 34 (as illustrated in FIG. 7), cutting may occur in either direction, pushing or pulling cutting element 44 through tissue. The sizes of shear slot 50 and cutting element 44 can be selected such that any removed tissue will not be allowed to adhere to the cutting element 44 due to the wiping action of the elements. For example, a cutting element 44 having a diameter of about 0.020 inch and fitting within a shear slot 50 with a clearance spacing of about 0.005 inch is suitable.

FIG. 3 shows one of many possible configurations of an alternative cutting element 52, which includes a pointed portion 54. One or more points may be employed to "bite into" or initiate contact with tissue and begin cutting without deflecting the tissue out of the path of the cutting element. Also, an angled or pointed cutting element allows for slicing tissue parallel to aperture 34 in a progressive fashion to reduce resistance of cutting. Cutting element 44 may also have a modified surface to be roughened or otherwise textured such as by being sand blasted, bead blasted, and/or machined roughened, which roughened profile can be useful to improve cutting efficiency by biting into the tissue to be resected.

Figure 22A:
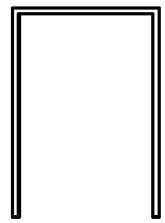
FIGS. 22A-22F illustrate various wire cutter configurations.
Figure 22B:
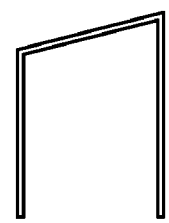
Figure 22C:
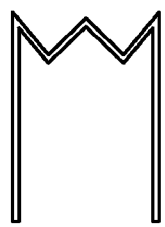
Figure 22D:
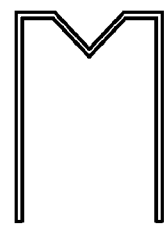
Figure 22E:
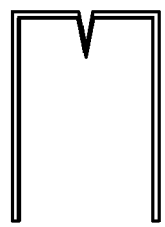
Figure 22F:
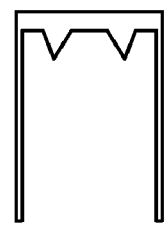

FIGS. 22A-22F show various wire cutter configurations. FIG. 22A illustrates a rectangular wire for providing initial cutting across the full width of the wire. FIG. 22B illustrates an angled cutting wire for initiating cutting at one corner of the wire, and for progressively engaging more tissue as the cutting wire is advanced along the length of the aperture 34. FIG. 22C illustrates a multiple point wire for providing multiple points of contact with tissue. FIG. 22D illustrates a single point or notch for providing single point contact upon initial tissue engagement. FIG. 22E illustrates a relatively sharp single point cutter for relatively high initial current density and mechanical penetration. FIG. 22F illustrates a wire cutter having a flattened (as opposed to circular cross-section) blade which can have a sharpened edge and points for cutting tissue with or without RF energy.

Figure 21:
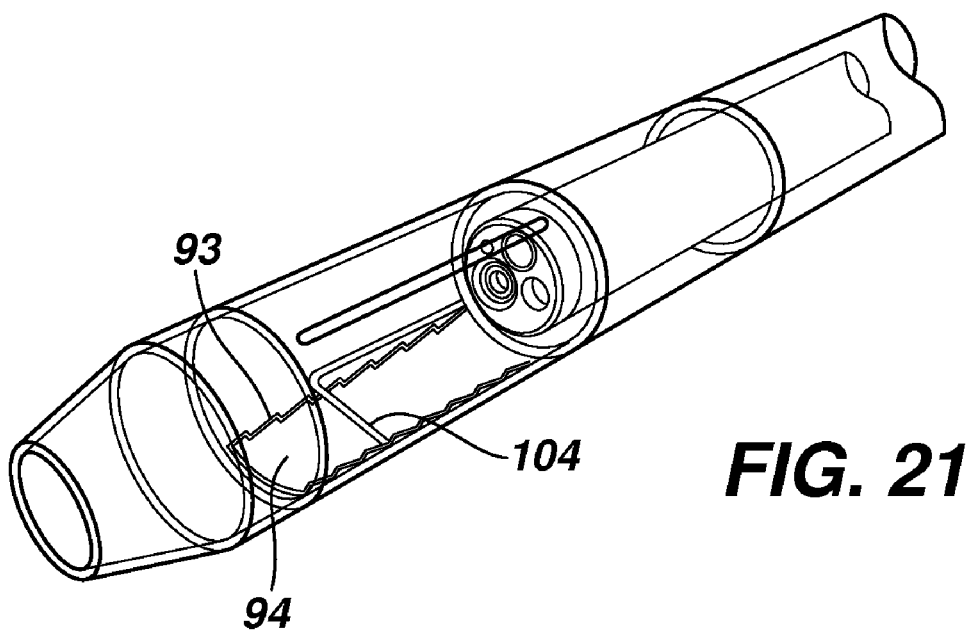
FIG. 21 is a schematic illustration of an embodiment of the device of the present invention including a tissue receiving aperture having serrated side edges.

Serrated edges can provided along the perimeter of a tissue receiving aperture. The textured surface provided by serrated aperture edges can provide for better gripping of the tissue during cutting. FIG. 21 illustrates a tissue receiving aperture having serrated edges.

In order to cut a mucosal layer of tissue from the alimentary canal of a patient for external study, the mucosal layer and sub-mucosal layers are typically separated somewhat from a muscularis layer of tissue by injecting a saline solution between them. This is commonly done by extending an injection needle through working channel 32 of endoscope 24 to contact and penetrate the target tissue.

In one embodiment, the present invention can provide an improved device and method for injecting saline solution. In the embodiments shown in FIGS. 1, 2, and 7-14, support 38 has secured therein a flexible sheath 56 for an injection needle 58. Sheath 56 can extend along side endoscope 24 to a handle, not shown, which is operated to deliver saline solution thru a hollow cable connected to injection needle 58. The hollow cable can be slidable within sheath 56 so that needle 58 may be extended beyond the fixed end of sheath 56 to engage mucosal tissue adjacent aperture 34. Sheath 56, which can be fixedly attached to cutter support 26, serves as a needle guide that is supported on the cutter support 26. Sheath 56 can enable the operator of the injection needle to control its position more accurately (in order to avoid penetrating the muscularis tissue) than when a needle and a sheath are operated through an endoscope's working channel.

Injection needle 58 can be used to deliver saline solution 60, as shown in FIGS. 10-13, through mucosal tissue 62 and sub-mucosal tissue 64 only. These softer tissues separate from stiffer muscularis tissue 66 when saline solution 60 is introduced. After injection, the needle is withdrawn from the tissue. Needle 58 and sheath 56 are shown in FIG. 2 in a retracted position extending through support 38 and angled toward aperture 34, in a plane which generally bisects aperture 34 and is centered between wire slots 40.

Tissue is drawn into aperture 34 by means of vacuum from a vacuum source, not shown, external to the patient's body. A suitable vacuum source can provide a vacuum of about 50 to 250 mm hg. Vacuum can be drawn through working channel 32 in endoscope 24. Air is drawn from the patient's alimentary canal, causing the canal to close down around cutter support 26 and bring tissue layer 62 in contact with the side of cutter support 26 where the tissue engages aperture 34. Vacuum communicated through the working channel 32 of the endoscope 24 and then through the openings in the stop plate 36 draws tissue layer 62 against stop plate 36 as air flows through the openings in the stop plate 36 to the opposite side of stop plate 36 where the distal end 22 of endoscope 24 can be positioned.

Although FIG. 2 shows a circular cross-section for cutter support 26, a flattened oval or other shape may enable an aperture to be wider for cutting a larger sample of tissue. Similarly, while aperture 34 is shown as a generally rectangular shaped opening on a cylindrical surface, other aperture shapes can be employed, including without limitation oval, circular, and polygonal.

Figure 4:
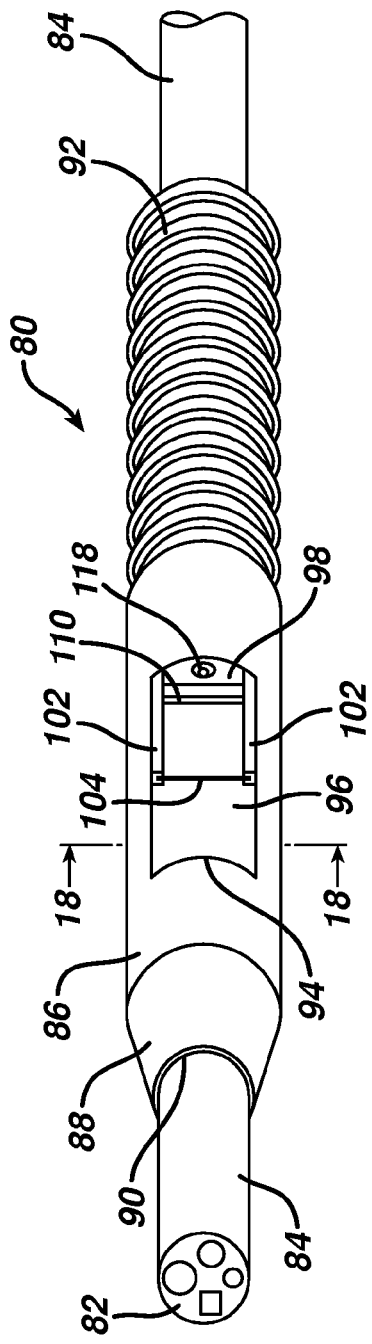
FIG. 4 is a perspective view of an alternative cutting device, showing a flexible overtube slidable along and rotatable about an endoscope.
Figure 6:
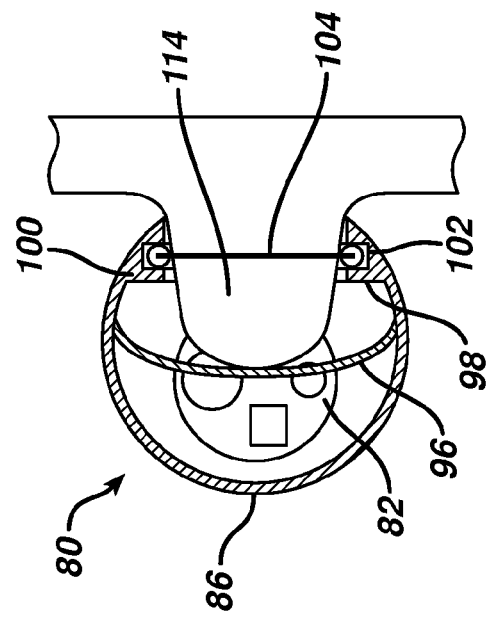
FIG. 6 is a cross-sectioned end view similar to FIG. 5, showing internal features in a different position by virtue of a tissue bleb sucked into an aperture in the overtube.
Figure 5:
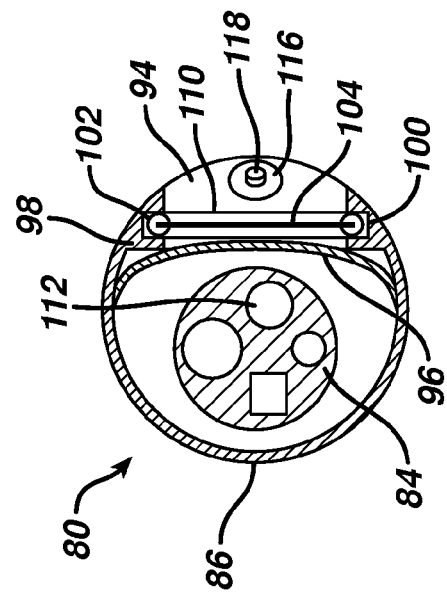
FIG. 5 is a cross-sectioned end view of the flexible overtube of FIG. 4, taken along section line 18-18, showing a circular embodiment of the cutter support and its internal features.

FIGS. 4-6 illustrates an alternative embodiment of a cutting device 80 of the present invention. In FIGS. 4-6, an endoscope is not fixedly attached to a cutting device 80. Instead, the cutting device 80 can comprise an overtube 86. The overtube can slide along an endoscope and rotate about the endoscope. Such an embodiment can permit closer access by the distal end of the endoscope to target tissue for examination and/or manipulation before or after mucosal tissue cutting. Alternatively, the cutting device and overtube can employ integral vacuum lines and visualization means (e.g. ccd camera) so that the cutting device and overtube can be used independently of an endoscope.

In FIG. 4, cutting device 80 is shown having a distal end 82 of a commercially available endoscope 84 extended therethrough. Endoscope 24 may be made by Olympus Optical, having an outside diameter of about 0.2 to 0.7 inches. Cutting device 80 has a flexible cylindrical overtube 86 slidably disposed along the length of the endoscope perimeter along parallel longitudinal axes. Overtube 86 can be relatively short and rigid, or can be flexible enough to conform to the articulations of flexible endoscope 84. Overtube 86 can have has at a distal end a flexible conical member 88, which provides for a smooth entry of cutting device 80 into the alimentary canal of a patient. Conical member 88 can be made of a flexible polymer such as PVC, PET, etc., and it has an open outer end 90 about 0.3 inches in diameter. The opening in the outer end can expand or be enlarged upon application of force so that endoscope 84 may extend therethrough. Conical member 88 can also be made of flexible polymer, and can be integral with overtube 86, or attached to overtube 86, such as by threading it onto overtube 86, by polymer welding, by snap-fit, or by other means. Conical member 88 cab be coaxial with overtube 86, whereas a longitudinal axis of endoscope 84 may be offset from a longitudinal axis of overtube 86, as shown in FIG. 2. The flexibility of the conical member 88 allows distal advancement of the endoscope to deflect the open end so that the endoscope is able to pass through the open end of member 88.

Overtube 86 can have a smooth outer diameter of about 0.40 to about 0.80 inches and a length of about 0.7 to 2.0 inches. The overtube 86 can be disposed at the distal end of a elongated, flexible tube or sleeve. In FIG. 4, the proximal end of the overtube 86 is molded or otherwise connected a flexible sleeve for receiving an endoscopic therethrough, which sleeve can be in the form of an elongated, corrugated tubular portion 92. Alternatively, the tubular portion 92 can be generally smooth. Tubular portion 92 can have an internal diameter sized to receive an endoscope therethrough, and tubular portion 92 can have a length at least about the length of the portion of the endoscope which is inserted into the patient. Corrugated portion 92 can have generally the same outside diameter as overtube 86. It may be connected to the overtube similar to the conical member, and shrink wrap material may be added at the connection to seal the corrugated portion to the overtube. In one embodiment, the flexible, elongated corrugated portion 92 can have a length of between about 2.7 feet and about 4.0 feet. In one embodiment, the internal diameter of the tubular portion 92 can be greater than 0.15 inch and less than about 0.85 inch, and more particularly between about 0.30 to about 0.75 inch.

Overtube 86 has a rectangular tissue receiving aperture 94 along one side, which is about 0.80 inches long and about 0.40 inches wide. A flexible stop plate 96 can be disposed just inside aperture 94. Stop plate 96 can be fastened to the inner wall of overtube 86 or otherwise disposed in aperture 94 such that stop plate 96 is able to toggle between (or otherwise assume) two different configurations. Two opposite edges of the stop plate 96 can be joined directly or indirectly along their lengths to the overtube 86, while the two opposite end edges of the stop plate can remain free and unconnected to other portions of the device to facilitate movement of the stop plate from one configuration to another. In one embodiment Stop plate 96 can have a width greater than a chord length across the overtube where stop plate 96 is mounted so that stop plate 96 is bowed (or otherwise deflected or deformed) in a generally arcuate fashion toward aperture 94 or away from aperture 94. In one embodiment, the flexible stop plate 96 is biased to bow toward aperture 94 to enable endoscope 84 to pass over it on an opposite side. In such an embodiment, stop plate 96 can be formed of a thin flexible material, such as PVC, PET or other flexible polymer. Stop plate 96 can have a thickness of less than about 0.05 inches, and can extend longitudinally beyond both ends of aperture 94.

The outwardly facing surface of stop plate 96 can include a portion which is conductive and which can serve as a ground or other pole of a electrical cutting circuit. In one embodiment, stop plate 96 has a conductive ink applied to one surface (e.g. the outwardly facing surface) so that it may serve as a grounding plate for RF heating of a cutting element as described for cutting device 20. Alternatively, an electrically conductive surface may be co-extruded on the stop plate 96, or the stop plate may be made of thin bio-compatible metal.

Overtube 86 can have a support 98 molded therein, which contains rectangular wire guide slots 100 between stop plate 96 and aperture 94. Wire guide slots 100 are sized for insulating sleeves 102 to slide longitudinally therein, just outside the width of aperture 94. Insulating sleeves 102 surround two wires that extend from an RF heating source (not shown) to distal ends of slots 100 near conical member 88, where they are attached to a heatable cutting element 104. Cutting element 104 extends from the sleeves 102 across aperture 94. As wires and sleeves 102 are slid parallel to the longitudinal axis of overtube 86 within slots 100, cutting element 104 passes across aperture 94 in order to cut tissue of a patient drawn into aperture 94, similar to the operation of cutting device 20. Cutting element 104 can be the same as that described for cutting element 44 or cutting element 52 above.

Cutting element 104 may be heated by a number of heating means including conduction and RF heating, which are commonly known in the endoscopic cutting art. Wire sleeves 102 are made of electrical insulating material such as Teflon, similar to insulating sleeves 42, and they extend along the outside of endoscope 84 to an insulated slide block, not shown. The slide block, similar to slide block 46, can be slidably attached to a handle located alongside an endoscope operating handle, such that the slide block is moved longitudinally to extend and retract sleeves 102 along endo scope 84 and through wire guide slots 100 so that cutting element 104 may be moved past the entire length of aperture 94 in overtube 86.

The heating of cutting element 104 may be the same as or similar to cutting element 44. In an RF heating embodiment, an RF grounding surface may be located within cutting device 80, for example by using a conductive tissue stop plate 96. Alternatively, a grounding plate separate from the stop plate 96 can be employed, but outside of the path of endoscope 84, so that the endoscope may freely pass through the overtube. A ground wire can be attached to the separate ground plate or to the stop plate, and the ground wire extends to a grounded location outside of the patient.

Supports 98 can also include, at each end of the wire slots 100, cutting element shear slots 110. The cutting element 104 can move into the shear slots 110 at the end of a cutting stroke in order to strip tissue from the cutting element. Such shear slots 110 can be the same as or similar to slots 50 of cutting device 20, and cutting may occur in two directions, either by pushing cutting element distally, or by pulling cutting element 104 proximally, through tissue.

FIGS. 4-6 show that overtube 86 has secured in support 98 a flexible sheath 116 for an injection needle 118. Sheath 116 extends along side endoscope 84 inside corrugated portion 92 to deliver saline solution thru a hollow cable connected to injection needle 58, in a similar manner to sheath 56 and needle 58, to engage mucosal tissue adjacent aperture 94. Needle 118 and sheath 116 are shown in FIGS. 4 and 5 in a retracted position extending through support 98 and angled toward aperture 94, in a plane centered within aperture 94, and between wire slots 100 and the aperture.

As shown in FIG. 6, when cutting device 80 is slid along endoscope 84 to a position where endoscope 84 no longer interferes with the toggling of stop plate 96, tissue may be drawn into aperture 94 by means of vacuum from a vacuum source, not shown, external to the patient's body. Vacuum is drawn through working channel 112 in endoscope 84. Air is drawn from the patient's alimentary canal, causing the canal to close down around overtube 86 and bring tissue 114 in contact with the side of overtube 86 where the tissue engages aperture 94. Vacuum draws tissue 114 against stop plate 96 and causes stop plate 96 to toggle away from, or otherwise deflect or deform away from, the aperture 94.

Although FIGS. 5 and 6 show a circular cross-section for overtube 86, a flattened oval or other shape may be used to permit an aperture to be wider for cutting a larger sample of tissue.

Cutting devices 20 and 80 are operated in a similar manner to remove a tissue sample. FIGS. 10-14 describe one method of using cutting device 20. FIG. 10 shows typical alimentary canal tissue, with mucosal layer 62 atop sub-mucosal layer 64 atop muscularis layer 66 brought into contact with aperture 34, by placement of the cutting device against the tissue or by a low level of vacuum from the endoscope working channel to close the alimentary canal wall against cutter support 26. In this position, needle 58 is extended from sheath 56 by pushing a hollow cable through the sheath, as described hereinbefore. Saline solution 60 is then injected into the tissue through the needle, preferably at a depth where sub-mucosal tissue and muscularis are separable, as is commonly understood in the endoscopic mucosal tissue cutting art. An amount of solution 60 is injected which separates the layers sufficient for cutting layers 62 and 64 without cutting layer 66.

Figure 11:
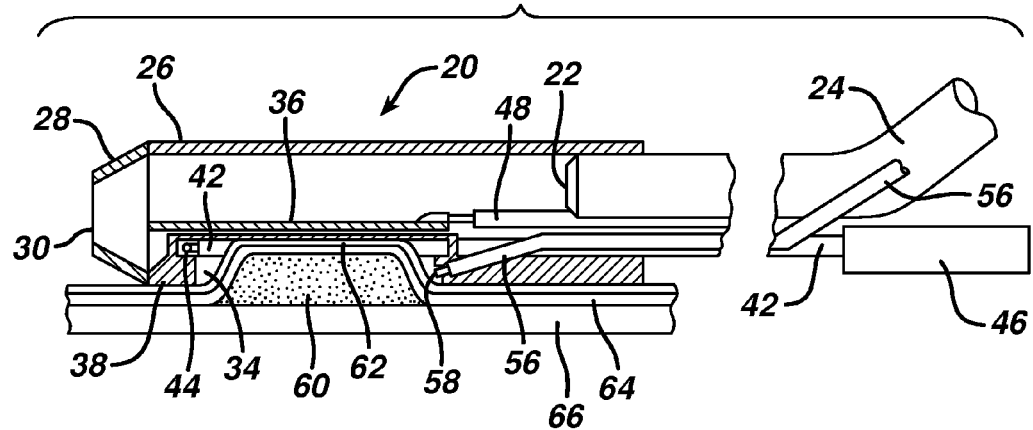
FIG. 11 is a cross-sectioned side elevation view similar to FIG. 10, showing the tissue bleb sucked into the aperture and against a stop plate, and the injection needle retracted.

FIG. 11 shows needle 58 withdrawn from the tissue and a higher level of vacuum sucking the tissue into aperture 34 and against stop plate 36. Cutting element 44 in this particular method, is shown extended to shear slot 50. RF energy is now delivered via wires surrounded by insulating sleeves 42 to cutting element 44, using conductive stop plate 36 as a ground for the RF energy path. Wire 48 connects stop plate 36 to an external ground, not shown. Cutting is ready to begin as cutting element 44 is rapidly heated to the desired temperature by controlling the level of RF energy.

Figure 12:
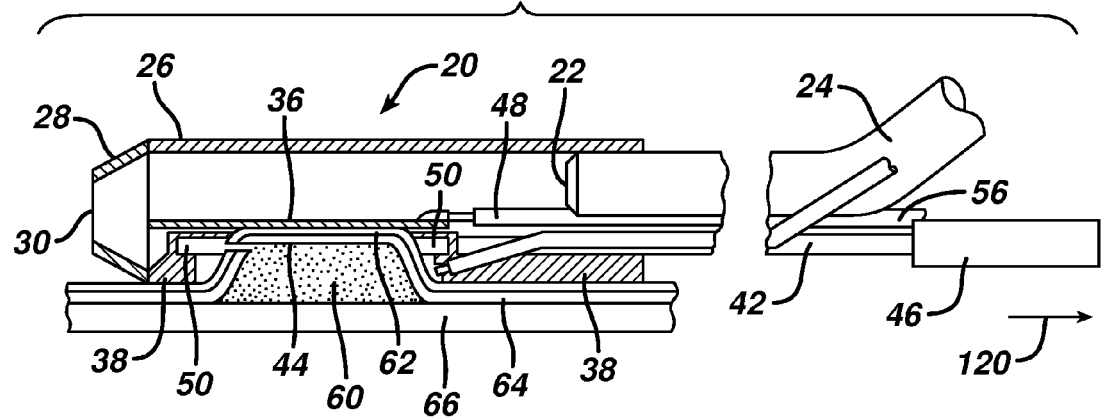
FIG. 12 is a cross-sectioned side elevation view similar to FIG. 11, showing a cutting element being retracted to cut through a first portion of a bleb, wherein mucosal and sub-mucosal tissue are cut from muscularis tissue.

FIG. 12 shows slide block 46 being moved along arrow 120 to pull cutting element 44 into tissue layers 62 and 64 and solution 60. Solution 60 can be drawn out by the vacuum, which vacuum can also be employed to secure the cut portion of tissue layers 62 and 64 against stop plate 36.

FIG. 13 shows slide block 46 being moved further along arrow 120 to complete the cut and shear tissue off cutting element 44 by pulling the cutting element into shear slot 50. Severed layers of tissue 62 and 64 continue to be held against perforated stop plate 36 by vacuum from endoscope 24 located on the opposite side of the stop plate. RF power can then be switched off. In FIGS. 12 and 13, stop plate 36 is not shown as being deformable. However, it will be understood that stop plate 36 can be made to be deformable as described above.

FIG. 14 shows cutting device lifted away from the remaining layers of tissue so that the cutting device may be withdrawn from the patient to examine the cut sample of tissue. A relatively lower level of vacuum can be employed to hold the cut tissue against the stop plate. The endoscope and cutting device may be rotated to a position such that the tissue sample is held against the stop plate by gravity when the vacuum is turned off. Alternatively, the cutting element (with not RF power applied) can be moved forward to a position similar to that of FIG. 12 to hold the cut tissue against the stop plate when the endoscope and tissue support 26 are manipulated to withdraw them from the patient. In another alternative, the cut tissue can be released from the stop plate and allowed to exit the aperture. Then the endoscope and cutting device can be partially withdrawn to where a gripper may be extended from a working channel of the endoscope through open distal end 30 to grasp the cut sample of tissue.

Figure 15:
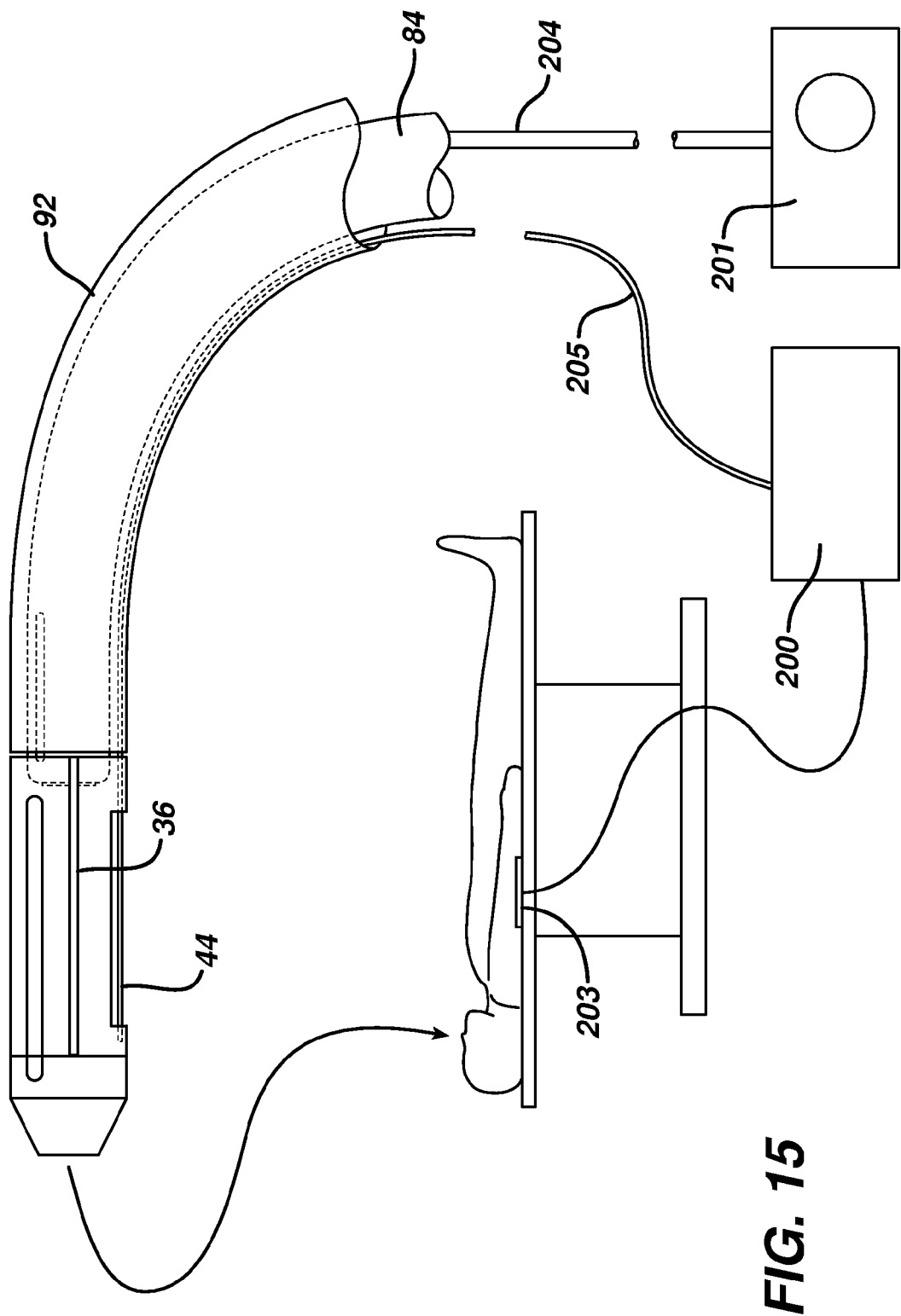
FIG. 15 is a schematic view showing a monopolar arrangement of the present invention.

FIG. 15 shows a monopolar arrangement of one embodiment of the present invention. The electrocautery generator 200 supplies the RF energy via a ground connected to the ground pad 203 at the patient's skin. The RF energy path 205 is connected to the RF cutting element 44/104. The vacuum pump 201 communicates with the cutter support 26/overtube 86 via a vacuum channel 204 which can be integral to the endoscope 84

Figure 16:
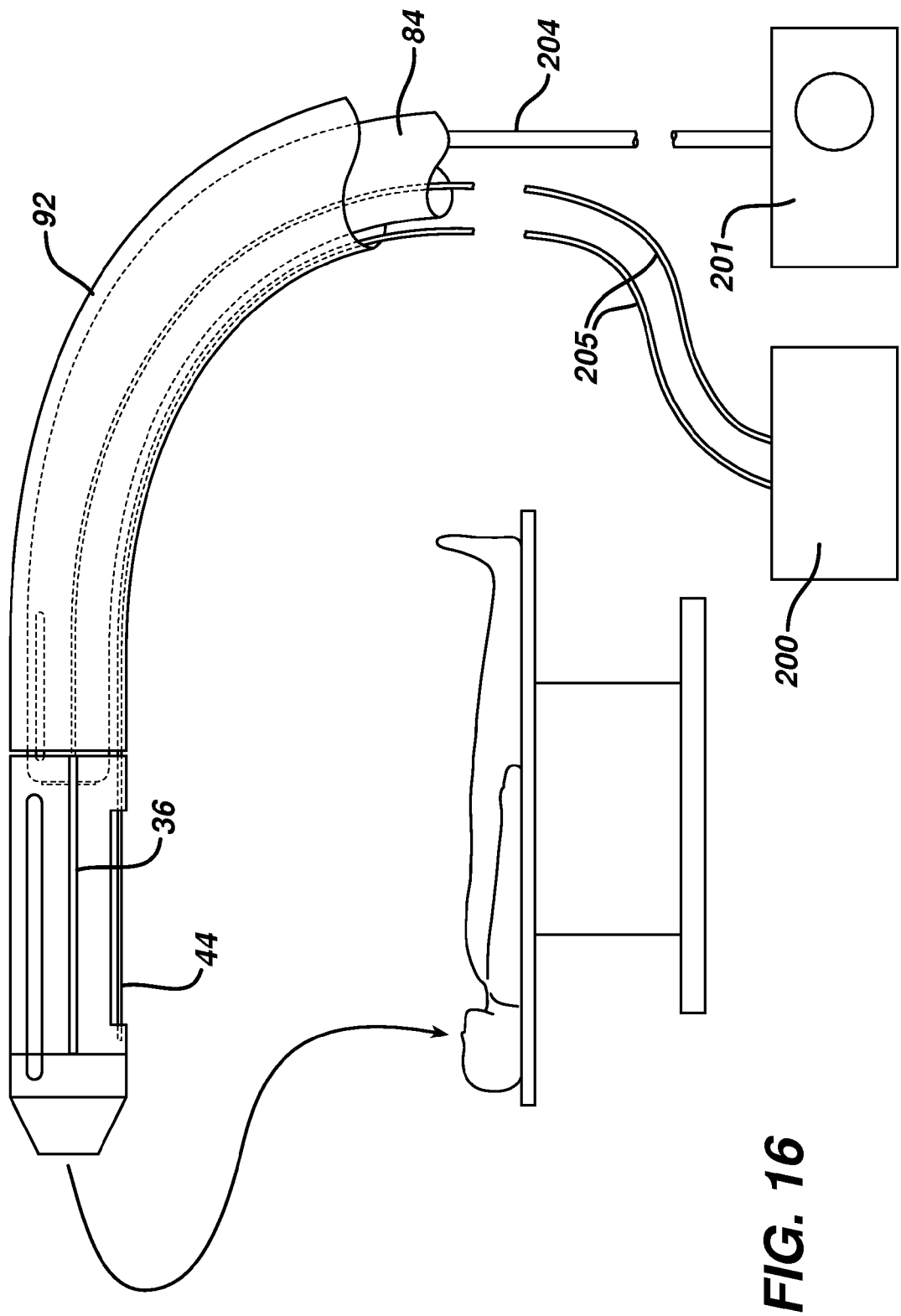
FIG. 16 is a schematic view showing a bipolar arrangement of the present invention.

FIG. 16 shows a bipolar arrangement of another embodiment of the present invention. The electrocautery generator 200 supplies the RF energy via energy paths 205. One polarity of the RF energy path 205 is connected to the RF cutting element 44/104 and the other polarity is connected to the stop plate 36/96. The vacuum pump 201 is connected to the support 26/overtube 86 via a vacuum channel 204 which can be integral to the endoscope 84.

Figure 17:
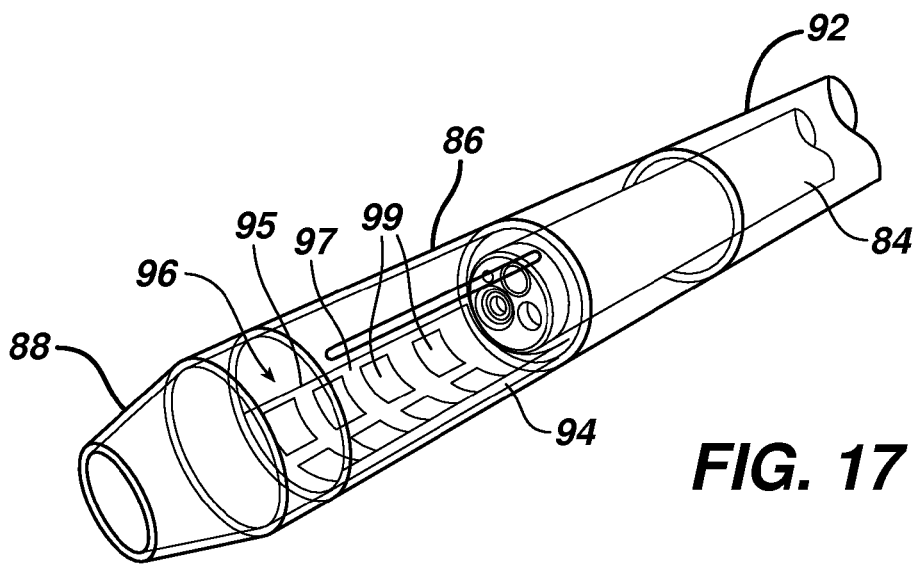
FIG. 17 is a schematic perspective illustration of a device of the present invention comprising a tissue stop having a foil conductor with rectangular openings therein, and showing the tissue stop in an outwardly bowed, generally arcuate configuration.
Figure 18:
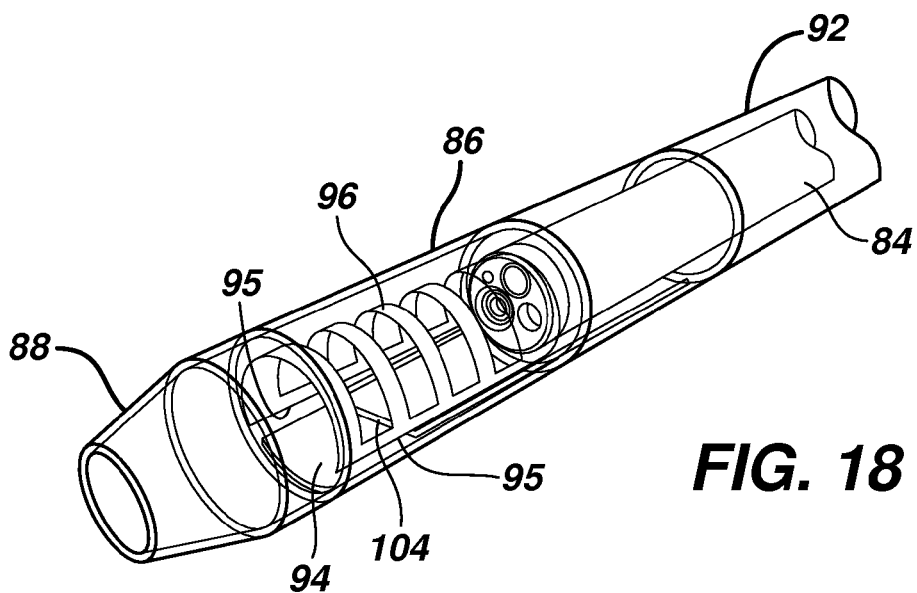
FIG. 18 is a schematic perspective illustration of the device of FIG. 17 showing the tissue stop deflected to a second configuration, such as by application of vacuum, to receive tissue and to permit passage of an endoscope thereby.

FIGS. 17 and 18 illustrate an embodiment of the present invention wherein the overtube 86 and elongated portion 92 can be transparent, and wherein the tissue stop plate 96 can be formed of a thin, transparent flexible polymeric material with a conductive grid 97 disposed on a surface of the tissue stop 96 facing the tissue receiving aperture 94. Grid 97 can define grid openings 99, which are generally rectangular in FIGS. 17 and 18. One or more openings 99 can be perforated for communicating vacuum therethrough if desired. Grid 97 can be formed of a suitable conductive material, such as a conductive metallic foil, or be painted or printed on with a conductive ink or coating. The conductive surface of the grid 97 can be between about 2 and about 10 times the conductive surface area of the cutter 104, and in one embodiment the conductive surface area of grid 97 can be about 4 times the conductive surface area of cutter 104.

The tissue stop 96 in FIGS. 17 and 18 can take on a first configuration in FIG. 17 (which permits passage of an endoscope thereby), and a second configuration shown in FIG. 18 when vacuum is applied (such as through endoscope 84) for limiting the amount of tissue drawn into aperture 94. The longitudinally extending sides 95 of tissue stop 96 can be fixed, such as by being joined to overtube 86. The proximal and distal ends of the tissue stop 96 can be unsupported and free to deform. The first and second configurations can be bowed, generally arcuate shapes, as shown in FIGS. 17 and 18. In one embodiment, the tissue stop 96 does not stretch or elongate in taking on the first and second configurations, but instead "toggles" or "snaps-through" from one configuration to the other.

A suitable tissue stop 96 can be formed from a section of a clear PET angioplasty balloon. The tissue stop 96 can be an arcuate segment cut from a generally cylindrical angioplasty balloon formed of PET. The arcuate segment can be cut from an angioplasty balloon cylinder having a diameter between about 10 and about 16 mm and a wall thickness of about 0.001 to about 0.002 inch. One suitable angioplasty balloon from which tissue stop 96 can be formed is a 10 mm diameter angioplasty balloon having a wall thickness of 0.002 inch (0.05 mm) available from Advanced Polymers of Salem, N.H. An arcuate segment can be cut from the angioplasty balloon to form the clear tissue stop 96. A thin metallic foil having a thickness of about 0.005 inch or less, such as a steel foil having a thickness of about 0.001 inch can then be applied to the surface of the stop 96 facing tissue receiving aperture 94, such as with an adhesive. Prior to attaching the foil to the stop 96, the foil can be cut to form a series of openings therethrough to provide the grid 97 shown in FIGS. 17 and 18.

Figure 19:
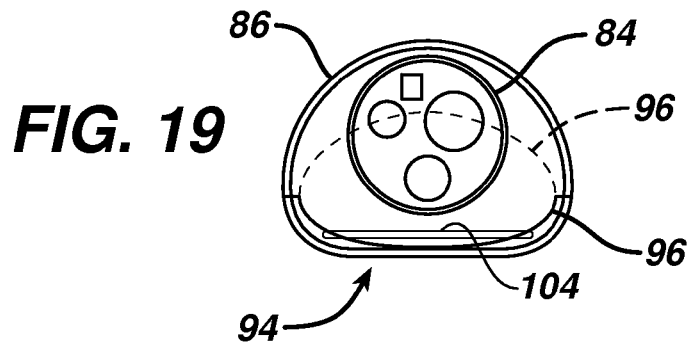
FIG. 19 is a schematic illustration an end view of one embodiment of the device of the present invention having an overtube that has a flattened or oval non circular cross-section, and depicting a tissue stop plate in first and second configurations, with the second configuration shown in phantom.

FIG. 19 illustrates a cross-sectional view of an overtube 86 having a noncircular cross-section, with a generally flattened outer surface portion in which tissue receiving aperture 94 is formed. An endoscope 84 is shown positioned in the overtube 86. The generally flattened outer surface portion is located on a bottom half of the overtube 86 as viewed in FIG. 19. Providing the tissue receiving aperture 94 in such a generally flattened surface portion can be useful in positioning the aperture 94 relative to tissue to be resected. FIG. 19 also shows first and second configurations of tissue stop 96, with the second configuration shown in phantom. In one embodiment, the overtube 86 can be formed in two shell-like halves, such as a generally semi-circular upper half and a non-circular lower half. The tissue stop 96 can be formed from a nonplanar, arcuate section of thin polymeric film material (such as a section of an angioplasty balloon described above), and the side edges of the arcuate tissue stop can be captured between the upper and lower halves of the overtube as the upper and lower halves are joined together, such as by adhesive or other suitable means. The proximal and distal ends of the tissue stop 96 can remain free and unsupported so that the tissue stop can snap through, toggle, or other wise deflect from the first configuration to the second configuration.

Figure 20:
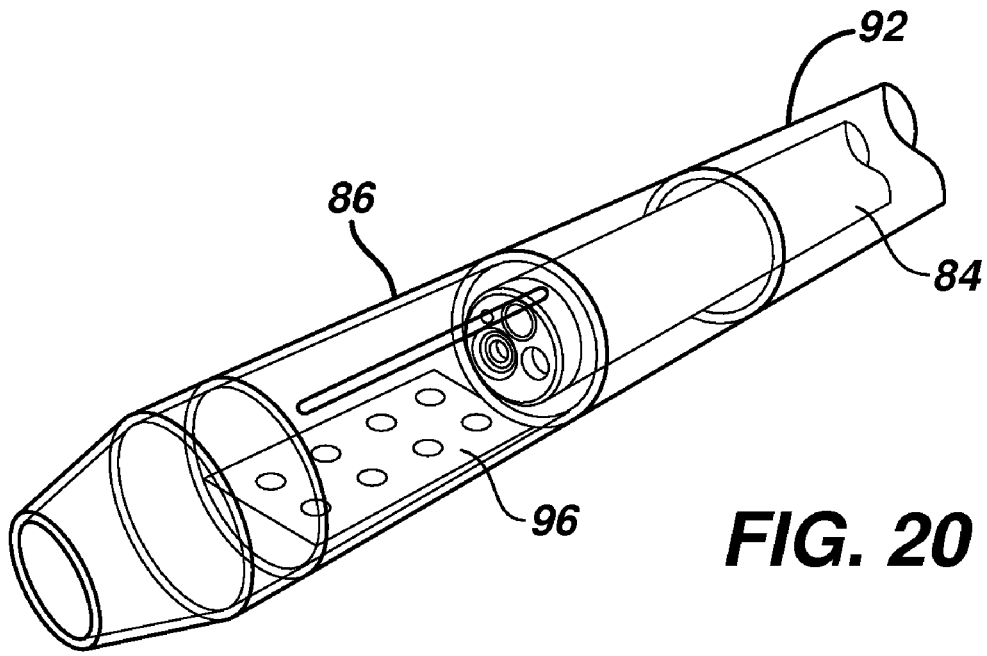
FIG. 20 is a schematic illustration of an embodiment of the device of the present invention including a transparent overtube, a transparent sleeve, and a perforated stop plate.

FIG. 20 illustrates an embodiment of the present invention having a transparent overtube 86 and transparent elongated sleeve portion 92. The tissue stop 96 is generally planar, with generally circular shaped vacuum openings therethrough. FIG. 21 illustrates an embodiment of the present invention wherein the overtube 86 has a tissue receiving aperture having serrated side edges 93 for assisting in grasping and cutting tissue with the cutting element 104. Tissue stop 96 is omitted from FIG. 21 for purposes of clarity in illustrating the side edges of aperture 94.

While the present invention has been illustrated by description of several embodiments, it is not the intention of the applicant to restrict or limit the spirit and scope of the appended claims to such detail. For instance, but without limitation, RF energy has been described as the tissue cutting method in the illustrated embodiments, but it will be understood that other tissue cutting modes, such as ultrasonic energy modes, mechanical cutting, and other methods could be employed in various embodiments of the present invention. Numerous other variations, changes, and substitutions will occur to those skilled in the art without departing from the scope of the invention. Moreover, the structure of each element associated with the present invention can be alternatively described as a means for providing the function performed by the element. Accordingly, it is intended that the invention be limited only by the spirit and scope of the appended claims.

What is claimed:

1. A medical apparatus comprising:
    an overtube for receiving an endoscope therein, the overtube comprising an open distal end and a side tissue receiving opening spaced proximally from the open distal end;
    an RF cutting element supported for movement across the tissue receiving opening, the RF cutting element is supported in at least one slot formed in a portion of the overtube; and
    a tissue stop disposed inwardly of the side tissue receiving opening, wherein the tissue stop comprises a plurality of vacuum openings therethrough.

2. The medical apparatus of claim 1 wherein the overtube is rotatable with respect to an endoscope received therein.

3. A medical apparatus comprising:
an overtube for receiving an endoscope therein, the overtube comprising an open distal end and a side tissue receiving opening spaced proximally from the open distal end wherein at least a portion of the overtube associated with the side opening has a non circular cross-section;
an RF cutting element supported for movement across the tissue receiving opening; and
a tissue stop disposed inwardly of the side tissue receiving opening, wherein the tissue stop comprises a plurality of vacuum openings therethrough.

4. A medical apparatus comprising:
an overtube for receiving an endoscope therein, the overtube comprising an open distal end and a tissue receiving opening spaced proximally from the open distal end;
a cutter support formed in a portion of the overtube associated with the side tissue receiving opening, the cutter support comprising a pair of guide slots extending generally parallel to side edges of the side tissue receiving opening; and
a cutting element supported in the guide slots for movement across the tissue receiving opening.

* * * * *